US012565622B2

(12) United States Patent
Gao et al.

(10) Patent No.: US 12,565,622 B2
(45) Date of Patent: Mar. 3, 2026

(54) PRODUCTION OF UREA FOR DIESEL EXHAUST FLUID

(71) Applicant: Stamicarbon B.V., Sittard (NL)

(72) Inventors: Chuanbo Gao, Sittard (NL); Khaled Elbassyouni, Sittard (NL); Lambertus Wilhelmus Gevers, Sittard (NL)

(73) Assignee: Stamicarbon B.V., Sittard (NL)

( * ) Notice: Subject to any disclaimer, the term of this patent is extended or adjusted under 35 U.S.C. 154(b) by 0 days.

(21) Appl. No.: 19/105,163

(22) PCT Filed: Sep. 6, 2024

(86) PCT No.: PCT/NL2024/050486
§ 371 (c)(1),
(2) Date: Feb. 20, 2025

(87) PCT Pub. No.: WO2025/053755
PCT Pub. Date: Mar. 13, 2025

(65) Prior Publication Data
US 2025/0263614 A1 Aug. 21, 2025

(30) Foreign Application Priority Data
Sep. 8, 2023 (EP) ..................................... 23196233

(51) Int. Cl.
*C10L 1/22* (2006.01)
*B01J 3/04* (2006.01)
*C07C 273/04* (2006.01)

(52) U.S. Cl.
CPC . *C10L 1/22* (2013.01); *B01J 3/04* (2013.01); *C07C 273/04* (2013.01); *C10L 2200/0446* (2013.01); *C10L 2290/56* (2013.01)

(58) Field of Classification Search
CPC ............... C10L 1/22; C10L 2200/0446; C10L 2290/56; B01J 3/04; C07C 273/04
See application file for complete search history.

(56) References Cited

U.S. PATENT DOCUMENTS

2017/0204054 A1* 7/2017 Mennen ................ C07C 273/16

FOREIGN PATENT DOCUMENTS

| | | |
|---|---|---|
| WO | 2006096048 A1 | 9/2006 |
| WO | 2008092647 A1 | 8/2008 |
| WO | 2016153354 A1 | 9/2016 |
| WO | WO-2019093891 A1 * | 5/2019 ........... B01D 5/0054 |
| WO | 2021156024 A1 | 8/2021 |
| WO | 2023158303 A1 | 8/2023 |

OTHER PUBLICATIONS

International Search Report and Written Opinion mailed Jan. 15, 2025 for the corresponding PCT International Patent Application No. PCT/NL2024/050486 (12 pages).

* cited by examiner

*Primary Examiner* — Latosha Hines
(74) *Attorney, Agent, or Firm* — Leason Ellis LLP

(57) ABSTRACT

Disclosed is a process for the production of an aqueous urea solution suitable for use as a Diesel Exhaust Fluid (DEF), wherein a condensate of off-gas obtained from further purifying an aqueous urea stream in a treatment section adapted to produce DEF, is sent to an LP dissociation section, thereby the removal of ammonia therefrom. This enables water obtained from such condensate to be recirculated to the DEF purification section, and prevents an unwanted build-up of water in recirculation to urea synthesis.

18 Claims, 1 Drawing Sheet

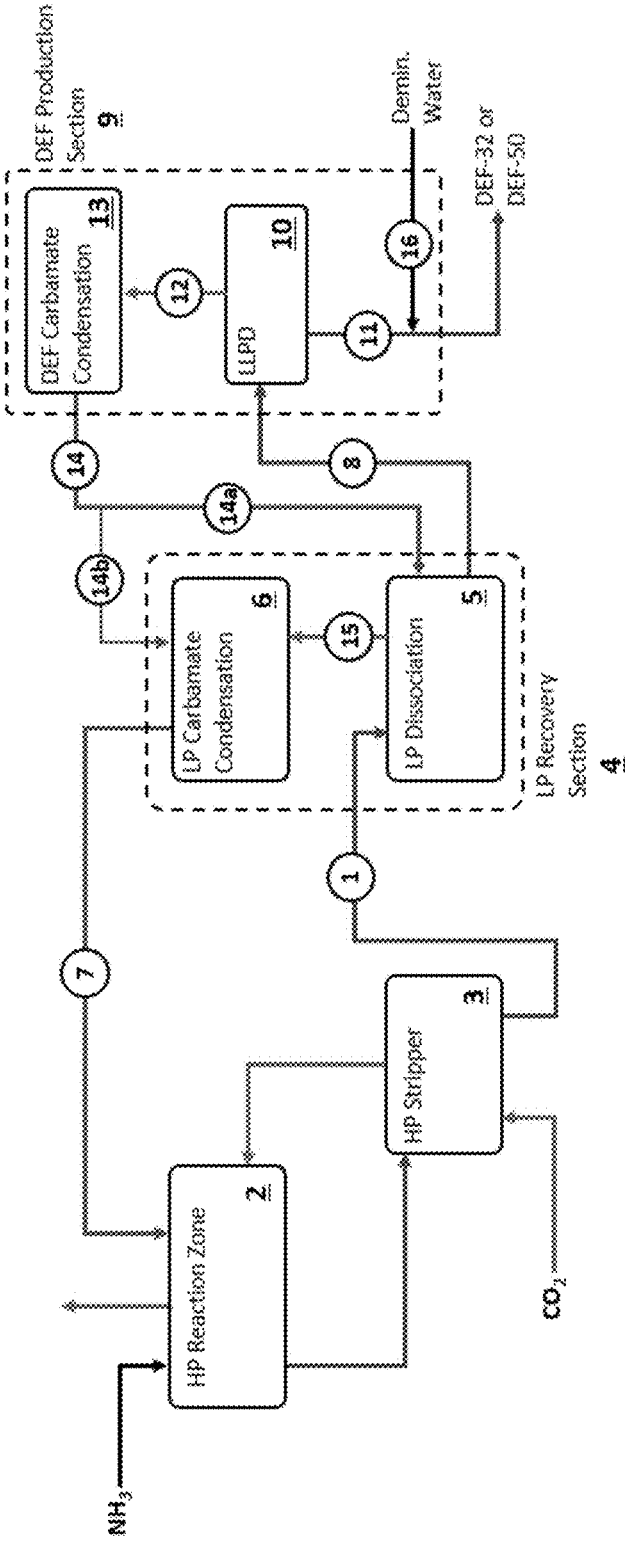

PRODUCTION OF UREA FOR DIESEL EXHAUST FLUID

CROSS-REFERENCE TO RELATED PATENT APPLICATIONS

This application is a U.S. National Stage Application under 35 U.S.C. § 371 of International Patent Application No. PCT/NL2024/050486 filed Sep. 6, 2024, which claims the benefit of priority of European Patent Application numbers 23196233.3 filed Sep. 8, 2023, all of which are incorporated by reference in their entireties.

FIELD OF THE INVENTION

The invention is in the field of the production of urea, and in particular pertains to a method for the production of a urea solution suitable for the abatement of $NO_x$ in combustion engine exhaust gases, for example exhaust gases produced from Diesel engines (DEF: Diesel Exhaust Fluid). The invention also pertains to a plant for carrying out the method, and a method of modifying a plant.

BACKGROUND OF THE INVENTION

Urea is generally produced from ammonia and carbon dioxide. It can be prepared by introducing an ammonia excess together with carbon dioxide at a pressure between 12 and 40 MPa and at a temperature between 150° C. and 250° C. into a high pressure (HP) urea synthesis section. Typical urea production plants further comprise one or more recovery sections operating at pressures of in a medium pressure (MP) range of typically 1-10 MPa and/or a low pressure (LP) range of typically 0.1-1 MPa (1-10 bar). In the one or more recovery sections, the aqueous urea solution obtained from the synthesis section is subjected to one or more downstream steps serving so as to recover and recirculate unreacted ammonia and carbon dioxide. In the event of more than one MP and/or LP recovery sections, such sections can be placed in series, in parallel, or both.

The recovery of ammonia and carbon dioxide at MP and/or LP generally involves the dissociation of ammonium carbamate resulting in a further purified urea solution and a gas stream. The gas stream is typically condensed in a carbamate condenser of the applicable recovery section, resulting in an aqueous carbamate solution that is typically recycled to the urea synthesis section.

Downstream of the recovery section or sections generally an evaporation section is present. Therein the urea concentration in said further purified urea solution is further increased by the evaporation of water, resulting in a highly concentrated solution that is generally referred to as a urea melt. The urea melt is typically sent to a finishing section, in which it is brought into a desired solid, particulate form, generally involving techniques such as prilling, granulation, or pelletizing.

In the evaporation section the amount of ammonia remaining in the process condensate thereof, particularly resulting from entrained urea, is still too high to be directly released into the atmosphere, typically 2-3 wt. %. This requires appropriate treatment, e.g. involving hydrolysis of urea and desorption of ammonia, in a wastewater treatment unit.

An interesting urea product is a solution for NOx abatement such as used in selective reduction, which may be a non-catalytic thermal process or a selective catalytic reduction (SCR) process. An example of a solution for SCR is diesel exhaust fluid (DEF), which term is used in description to generally refer to urea solutions for NOx abatement.

DEF as used for cars and trucks, is a 32.5 wt. % urea solution in purified (typically demineralized) water with a composition that has maximum 0.3 wt. % biuret and maximum 0.2 wt. % of alkalinity as ammonia. For marine applications, DEF has a 40 wt. % concentration. Optionally DEF is produced in higher concentrations, for example at 50 wt. % or higher, for transportation and off-site dilution. DEF is marketed under the (commercial) trade names Ad-Blue®, Air1®, Arla 32 and AUS-32 and is injected in the tail gas of combustion engines to capture $NO_x$ to prevent it from escaping to the atmosphere. The purpose of the DEF is to convert the $NO_x$ into a harmless form of nitrogen. Urea in fact acts as a safe way to provide ammonia as a reactant in a process to convert the $NO_x$. In this process urea is initially converted into ammonia and carbon dioxide, and the ammonia reacts with $NO_x$ into inert molecular nitrogen ($N_2$) and water. Reduction of $NO_x$ from combustion engines is widely applied as $NO_x$ is one of the main sources for environmental pollution indicated for global warming such as the Global Warming Potential (GWP), Tropospheric Ozone Formation Potential (TOFP) and Ozone Depletion Potential (ODP).

An early method for the production of Diesel Exhaust Fluid (DEF) is by dissolving a solid urea product in demineralized water. An improved process, disclosed in WO2006/096048, is to use a urea aqueous solution obtained directly from or after a recovery section of a urea production plant, and to dilute said urea aqueous solution with water to obtain the desired solution. I.e., with reference to a regular urea melt plant the urea aqueous solution intended for the production of DEF is obtained at a position upstream of where otherwise said solution would be subjected to further concentrating the produced urea, and finishing steps to obtain a solid product.

The foregoing method reduces the amount of water that is to be evaporated, and sent to the corresponding wastewater treatment. It will also be understood, however, that a urea aqueous solution so obtained may contain relatively high levels of ammonia which exceed the specification for the final DEF product.

To this end, WO2006/096048 discloses that the ammonia level (as free ammonia or in the form of ammonium carbamate) in the solution may be reduced by subjecting the urea aqueous solution to dissociation, for example by the addition of heat or the reduction of pressure, optionally with the addition of a stripping medium or a combination of the foregoing. A similar treatment in a DEF purification section, serving to produce an aqueous urea solution meeting the stringent requirements for DEF, is disclosed in various references relating to different aspects of urea production for DEF, including WO2019/93891 and WO2023/158303. Generally, such DEF purification treatment results in a purified solution, and a gas stream comprising $NH_3$ and $CO_2$. With reference to, inter alia, WO2019/93891 and WO2023/158303, the latter gas stream is typically sent to a dedicated LP carbamate condenser of the DEF purification section, although it can also be sent to a different LP carbamate condenser.

The condensate, i.e. aqueous carbamate solution, is sent to the LP carbamate condenser (usually referred to as LPCC) of the recovery section applied in the urea production process. Sending said DEF purification condensate to the LPCC generally serves to optimize the total carbamate recycle to urea synthesis.

The foregoing method allows DEF to be produced in a urea production plant that also is capable of producing finished solid urea product such as granules, prills, or pellets, or urea melt for melamine production, or urea solution that can be used for making urea ammonium nitrate (UAN). Alternatively, it allows providing a dedicated production plant for DEF, not comprising a finishing section. The production of DEF can also be combined, in a single plant or in combined plants, with the production of other urea products, such as urea ammonium nitrate (UAN), as disclosed, inter alia, in WO2016/153354.

DEF has to meet very strict purity specifications. Preferably this is in accordance with a norm such as ISO 22241-1:2006 for vehicle application, or ISO 186111-1:2014 for rail and marine application, notably in respect of biuret and ammonia. Thus, a typical DEF purification treatment requires a still further dissociation of still present unconverted ammonium carbamate. Yet, the conditions for such dissociation are limited in the sense that higher temperatures will promote biuret formation. As a result, such dissociation is generally conducted in a section operating at an LP level or at a reduced pressure level, such as 0.1 bara to 2 bara, preferably sub-atmospheric.

Both in view of process economy and environmental safety, it is generally desired to recirculate any recovered ammonia and carbon dioxide as a feed to urea synthesis as a carbamate solution. However, at lower pressures, and consequently lower condensation temperatures, a relatively higher amount of water needs to be present in the carbamate solution in order to prevent dissolved ammonium carbamate from crystallizing. Yet, the corresponding recirculation of additional water to urea synthesis is undesirable, in view of the adverse effect that the presence of water has on the reaction equilibrium of the conversion of ammonium carbamate into urea and water.

At the same time, DEF being essentially a dilute aqueous solution of urea, it requires a considerable amount of water as part of the product. It will be understood that any dilution with water should not result in introducing further impurities in the DEF product. Such dilution therefore is typically carried out with demineralized or distilled water.

Accordingly, a challenge in the field is to provide an effective management of the aqueous streams involved in DEF production. This holds for dedicated DEF plants as well as for plants combining DEF production with that of solid urea and/or combined urea products.

SUMMARY OF THE INVENTION

In order to better address one or more of the foregoing desires, the invention, in one aspect provides a process for the production of an aqueous urea solution suitable for use as a Diesel Exhaust Fluid (DEF), the process comprising reacting ammonia and carbon dioxide in a high pressure (HP) synthesis section under urea-forming conditions, thereby obtaining a urea synthesis solution; subjecting the urea synthesis solution to a recovery treatment so as to remove remaining ammonia and carbon dioxide therefrom, said treatment comprising dissociation in a low pressure (LP) dissociation section, resulting in an aqueous urea product stream and an LP dissociation off-gas; subjecting said LP dissociation off-gas to condensation, thereby obtaining an LP condensate; recirculating said LP condensate as a feed to urea synthesis; subjecting the aqueous urea product stream to removal of further ammonia in a DEF purification section, thereby obtaining a purified urea solution and a DEF purification off-gas; subjecting the DEF purification off-gas to condensation thereby obtaining a DEF purification condensate; adjusting the water content of the purified urea solution, thereby obtaining a DEF product solution; wherein the process comprises subjecting at least part of the DEF purification condensate to removal of ammonia in the LP dissociation section.

In another aspect, the invention presents a plant for the production of an aqueous urea solution suitable for use as a Diesel Exhaust Fluid (DEF), said plant comprising a high pressure (HP) synthesis section configured to subject ammonia and carbon dioxide to reaction under urea-forming conditions, thereby obtaining a urea synthesis solution; downstream thereof and in fluid communication therewith, a low pressure (LP) recovery section configured to subject a passing urea solution to recovery of remaining ammonia and carbon dioxide contained therein, said LP recovery section comprising an LP dissociation section and an LP condensation section, said LP dissociation section comprising an inlet for a urea solution, said inlet being in fluid communication, optionally via an MP section, with an outlet for a urea synthesis solution from the HP synthesis section, an outlet for an aqueous urea product stream, and an outlet for dissociation off-gas, said outlet for dissociation off-gas being in fluid communication with a gas inlet of the LP condensation section, said LP condensation section having an outlet for LP condensate which outlet is in fluid communication with an inlet of the HP synthesis section; the plant further comprising a DEF purification section configured to subject the aqueous urea product stream to removal of further ammonia, said DEF purification section having an inlet for a liquid urea stream, which inlet is in fluid communication with the outlet for an aqueous urea product stream of the LP dissociation section, an outlet for a purified urea solution, and an outlet for DEF purification off-gas, said outlet for DEF purification off-gas being in fluid communication with an inlet of a DEF purification condensation section configured to subject the DEF purification off-gas to condensation, thereby obtaining a DEF purification condensate, said DEF purification condensation section having an outlet for said DEF purification condensate, which outlet is in fluid communication with an inlet of the LP dissociation section.

In a further aspect, the invention pertains to a method of modifying a pre-existing plant for the production of an aqueous urea solution suitable for use as a Diesel Exhaust Fluid (DEF), said pre-existing plant comprising a high pressure (HP) synthesis section configured to subject ammonia and carbon dioxide to reaction under urea-forming conditions, thereby obtaining a urea synthesis solution; downstream thereof and in fluid communication therewith, a low pressure (LP) recovery section configured to subject a passing urea solution to recovery of remaining ammonia and carbon dioxide contained therein, said LP recovery section comprising an LP dissociation section and an LP condensation section, said LP dissociation section comprising an inlet for a urea solution, said inlet being in fluid communication with an outlet for a urea synthesis solution from the HP synthesis section, an outlet for an aqueous urea product stream, and an outlet for dissociation off-gas, said outlet for dissociation off-gas being in fluid communication with a gas inlet of the LP condensation section, said LP condensation section having an outlet for LP condensate which outlet is in fluid communication with an inlet of the HP synthesis section; the plant further comprising a DEF purification section configured to subject the aqueous urea product stream to removal of further ammonia, said DEF purification section having an inlet for a liquid urea stream, which inlet is in fluid communication with the outlet for an aqueous urea product stream of the LP dissociation section, an outlet for a purified urea solution, and an outlet for DEF purification off-gas, said outlet for DEF purification off-gas being in fluid communication with an inlet of a DEF purification condensation section configured to subject the DEF purification off-gas to condensation, thereby obtaining a DEF purification condensate, said DEF purification condensation section having an outlet for said DEF purification condensate, which outlet is in fluid communication with the LP recovery section, the method comprising providing a fluid connection between an outlet for the DEF purification condensate of the DEF purification condensation section, with an inlet for a urea solution of the LP dissociation section.

BRIEF DESCRIPTION OF THE DRAWINGS

FIG. 1 is a schematic representation of the process of the invention, as conducted in plant according to the invention.

DETAILED DESCRIPTION OF THE INVENTION

The invention is based on the judicious insight that the LP dissociation section, from which the aqueous urea product stream is obtained that is subjected to said DEF purification, can also serve the purpose of removing ammonia from the condensate obtained from said DEF purification. Effectively, by sending at least part of the DEF purification condensate to the LP dissociation section, ammonia will be removed therefrom with the LP dissociation off-gas.

With ammonia thus being preferentially removed in the LP dissociation section, the larger part of the water contained in said DEF purification condensate does not end up in the LP condensation section, and therewith it also does not end up in urea synthesis. This reflects an improvement as compared to the prior art processes in which the DEF purification condensate is sent to an LP carbamate condenser. Moreover, as a synergistic benefit, the water which is thus prevented from ending up where it is in fact detrimental, ends up actually where the presence of water is desired, viz. in the DEF purification section as part of the aqueous urea product stream that is purified, and further diluted, to be obtained as DEF.

Where it is spoken of "DEF purification" this refers to the treatment of an aqueous urea stream by which a final amount of ammonia still contained therein is removed such that the urea solution resulting therefrom, when diluted to a concentration for it to be suitable as DEF, has an ammonia content not exceeding the corresponding specifications.

DEF is used in vehicles with diesel engines for $NO_x$ emissions abatement. The composition of DEF for vehicles is standardized in ISO 22241-1:2006. DEF for vehicles has about 32.5 wt. % urea (i.e. essentially the eutectic composition) and also has a very low concentration of impurities. The product urea solution can also be used e.g. for $NO_x$ abatement in industrial plants and in ships and trains. For $NO_x$ abatement used in rail and marine applications, about 40 wt. % urea solution is used according to ISO 186111-1: 2014. For $NO_x$ abatement for (fossil fuel) power plants, typically 50 wt. % urea solution is used. The term "DEF" is used in the present disclosure, also for the invention, to refer in particular to a urea solution suitable, adapted and/or identified for use in $NO_x$ abatement, e.g. urea solution according to any of said specifications, more in particular to urea solution according to ISO 22241-1:2006.

When making DEF, the concentration of urea is important in order to allow accurate dosing of the liquid to the SCR catalyst. The low concentration of organic impurities in DEF is important to avoid clogging and coke formation on the catalyst surface. The very low concentration of inorganic impurities in DEF, in particular of heavy metals, is important because these impurities contribute to poisoning of the SCR catalyst. The metals will accumulate on the catalyst and thereby reduce the lifetime of the catalyst.

The DEF purification will be conducted in a DEF purification section, as further discussed below. The DEF purification section will usually be part of a urea production plant, but it can also be built as a separate DEF production unit linked to a urea plant. The urea plant can be a dedicated DEF production plant, or it can be a plant capable of producing also other urea products, such as a urea melt, finished solidified urea products such as prills, granules, or pellets, and/or combined urea fertilizer products, such as urea ammonium nitrate or urea ammonium sulfate.

A first step of the process of the invention comprises reacting ammonia and carbon dioxide in a high pressure (HP) synthesis section under urea-forming conditions. Suitable urea synthesis technologies are known in the art, as reflects, e.g., in Ullmann's Encyclopedia of Industrial Chemistry (2012), chapter on Urea. With reference to the involvement, in the process of the invention, of an LP dissociation section, it will be understood that urea is synthesized by means of a process of the total recycle type, in which essentially all of the non-converted ammonia and carbon dioxide are recycled to urea synthesis. Specifically, this can be a so-called conventional recycle process or a stripping process. These processes are well-known to the skilled person, as are the corresponding plants. For the synthesis of DEF in a stripping plant, reference is made, e.g., to WO2006/096048 or WO2023/158303. For the synthesis of DEF in a conventional urea plant, reference is made to WO2019/93891.

In a stripping plant, the synthesis section includes a reaction zone, a stripper, and a condensation zone, forming a high-pressure loop. The output of the reactor is a reactor effluent which essentially is an aqueous solution of urea containing unreacted ammonia and carbon dioxide, mostly in the form of ammonium carbamate. The reactor effluent is heated in the stripper, possibly with the help of a gaseous stripping agent, to remove a gaseous stream containing ammonia and carbon dioxide. This gaseous stream emerging from the stripper is condensed in the condenser, possibly with the help of a solution recycled from a recovery section. The so obtained condensate is recycled to the reactor. The Stamicarbon $CO_2$-stripping process uses gaseous $CO_2$ as a stripping agent. Another stripping process uses gaseous ammonia as a stripping agent. The invention is not limited to any particular urea total recycle production process, e.g. the HEC process developed by Urea Casale, the ACES process developed by Toyo Engineering Corporation and the process developed by Snamprogetti. All of these processes, and others, may be used in the method of the invention.

The synthesis section is generally operated at high pressure (HP), i.e., a pressure in a range of from 12 to 40 MPa and at a temperature between 150° C. and 250° C. In a preferred embodiment, the reaction is conducted at a synthesis pressure of 130-150 bara. In a further embodiment, the entire HP synthesis section is operated at a pressure in the range of 130-150 bara.

As said, the process of the invention comprises subjecting the urea synthesis solution obtained from the synthesis section to a recovery treatment so as to remove remaining ammonia and carbon dioxide therefrom. Such remaining ammonia and carbon dioxide may be present in the form of ammonium carbamate that has not been converted into urea, and it may include ammonia and carbon dioxide as such, originating from either or both of unreacted feed reactants and a dissociated part of the unconverted ammonium carbamate. The recovery treatment may include one or more recovery stages at a recovery pressure lower than the synthesis pressure, to remove to a great extent said remaining ammonia and carbon dioxide from the urea synthesis solution, and to obtain a urea aqueous solution consisting essentially of urea and water, yet inevitably with still some residual reactants present. A recovery stage for example includes heating the solution to obtain dissociation of carbamate and condensing the off-gas thereby obtained into a carbamate-containing recycle solution. This solution may be recycled to the synthesis section, e.g. to the condenser of the synthesis loop.

Said recovery optionally involves one or more medium pressure (MP) stages, in which carbamate dissociation, optionally with stripping, is conducted at a medium pressure (MP), i.e., a pressure in a range of from 1-10 MPa. The one or more MP recovery stages may be conducted in an MP recovery section comprising, e.g., an MP scrubber or an MP flash and a condenser, or an MP heater integrated with an MP $CO_2$ stripper. The MP recovery stages can be in series and/or in parallel. Downstream of the MP recovery stage or stages, one or more low pressure (LP) recovery stages follow, generally involving a pressure in a range of from 0.1 MPa to 1 MPa, i.e., 1-10 bara.

As a final stage of recovery, the process of the invention comprises dissociation in a low pressure (LP) dissociation section. This section comprises at least one LP dissociator, typically a heat exchanger such as a shell and tube heat exchanger, and possible a combination of two or more dissociators, which may be the same or different. The LP dissociation section referred to in the present disclosure will generally be a single section, and generally one that is already present in a urea plant. It is conceivable, however, to operate two or more of such LP dissociation sections in parallel. In other words, in terms of equipment, e.g. one LP dissociator can be used to obtain the aqueous urea product stream to be sent to DEF purification, and another, parallel, LP dissociator can be used to receive the DEF purification condensate, and recycle the water obtained therefrom to the DEF purification section. The same holds for the optional presence of more than one LP condensation section, which all are part of the same carbamate recovery and recirculation loop. Additionally, it is conceivable to apply more than one carbamate recirculation loop, e.g., when modifying an existing plant in connection with the present invention.

The LP dissociation results in an aqueous urea product stream and an LP dissociation off-gas. Said off-gas comprises residual reactants ammonia and carbon dioxide, which eventually are recycled to urea synthesis. To this end, the process comprises subjecting the LP dissociation off-gas to condensation. This condensation takes place in an LP condensation section which comprises at least one LP condenser, and possibly two or more, e.g., in parallel. A condenser typically is a heat exchanger, such as a shell and tube heat exchanger. As a result of said LP condensation an LP condensate is obtained, which eventually can be recirculated as a reactant feed to urea synthesis.

The liquid part resulting from LP dissociation is an aqueous urea product stream which is relatively pure, but which is not yet suitable to meet the purity desired for DEF, let alone the purity as required according to DEF specifications such as referred to above. This particularly concerns the unwanted presence of ammonia. Generally, depending on any evaporation step that may still be included, said aqueous urea product stream will have a urea concentration of 20 to 95 wt. %, preferably 50 to 90 wt. %, more preferably 60 to 85 wt. %. In the event of a dedicated DEF plant, not also applied to produce a urea melt or parallel urea products such as UAN, an evaporation section does not need to be present in the urea plant. Without such a section present, or with obtaining the aqueous urea product stream from a position upstream of such evaporation section, or from by-passing such a section, the urea concentration will generally not exceed 77 wt. %.

It will be understood that in the event of having a urea concentration below that of the desired DEF concentration (such as, e.g. 32.5 wt. % for vehicle application or, e.g., 40 wt. % for marine and/or rail application), the step of adjusting the water content of the purified urea solution will involve removing water, typically by evaporation, rather than adding demineralized or distilled water.

As a general preference, the urea content of the aqueous urea stream is in a range of from 60 wt. % to 77 wt. %.

In order to produce DEF, the aqueous urea product stream is subjected to removal of further ammonia in a DEF purification section. This section operates to dissociate remaining ammonium carbamate therein, and remove the ammonia resulting therefrom, generally together with carbon dioxide.

The DEF purification possibly involves washing with carbon dioxide, as disclosed in WO 2008/092647. Generally, it is preferred that the DEF purification section does not involve heating to above 135° C., preferably not above 100° C., in order to prevent the formation of biuret, as this should otherwise have to be removed in view of applicable DEF specifications. Removal of biuret is referred to, e.g., in WO2021/156024, applying reverse osmosis to this end. Generally, therefore, the DEF purification will involve a further expansion of the aqueous urea product stream obtained from the LP dissociation section. Preferably, the DEF purification section is operated under a pressure up to 3 bara, preferably from 0.1 to 2 bara, such as 0.1. to 1.0 bara, preferably sub-atmospheric, more preferably at 0.2 to 0.9 bara, still more preferably at 0.3 to 0.6 bara.

In particular the purification preferably removes excess ammonia, i.e. ammonia above the desired level, in particular above the desired alkalinity as $NH_3$ level. This removal ensures that the purified solution has sufficiently low alkalinity. Low alkalinity is important to avoid the risk of corrosion of equipment in contact with the DEF solution. Lower $NH_3$ content of the DEF solution advantageously reduces ammonia smell. The removal of ammonia generally involves transfer of $NH_3$ from the liquid phase to the gas phase.

The purification, preferably stripping, is preferably such that the purified solution, as obtained by said purification has an alkalinity as $NH_3$ of less than 0.20 wt. %, less than 1000 ppm, less than 500 ppm, or less than 200 ppm, all by weight, when at 32.5 wt. % urea, i.e. the alkalinity converted on the basis of water added or removed as necessary to have 32.5 wt. % urea, in other words said alkalinity levels are on the basis of 32.5 wt. % urea solution. Lower alkalinity is preferred.

In some embodiments, the purification involves reducing the alkalinity as $NH_3$ of a urea solution to be purified, by at least 50% or at least 90% or at least 99%, as relative percentage of the initial alkalinity as $NH_3$ value, by transfer of a corresponding amount of ammonia (in any form in the solution) to the gas phase. In the embodiment wherein the purification yields urea solution with an alkalinity as $NH_3$ of less than 0.2 wt. %, the initial urea solution can already have an alkalinity below the specified level, in which case the alkalinity as $NH_3$ is further reduced by the purification.

In some embodiments, the purification, such as stripping, involves dissociation of ammonium carbamate to $NH_3$ and $CO_2$, and transfer of this formed $NH_3$ from the liquid phase to the gas phase to remove the $NH_3$ from the solution, typically together with transfer of free $NH_3$ from the liquid phase to the gas phase. Typically, with such dissociation the alkalinity as well as the carbonate content (as $CO_2$) is reduced, for instance to a carbonate content (as $CO_2$) of said purified solution of less than 0.5 wt. % or less than 0.2 wt. %, or to less than 1000 ppm or less than 500 ppm by weight, on the basis of 32.5 wt. % urea solution.

The purification for example involves pressure reduction (i.e. reduction of the absolute pressure), heating, stripping, and combinations of these. In some embodiments the purification involves heating and/or pressure reduction without stripping.

The purification preferably comprises stripping. Stripping allows for reducing the purification temperature thereby advantageously reducing biuret formation. The stripping preferably involves contacting the urea solution in counter current flow with a gaseous stream. The gaseous stream typically has a lower partial vapour pressure of $NH_3$ than the urea solution that is in contact with the gas. The stripping preferably involves steam stripping. Air stripping can also be used. The steam stripping preferably involves contacting the aqueous urea solution in counter current flow with steam. The steam can be supplied from battery limit, e.g. from another plant such as from a utility plant. but preferably is LP steam produced in a condenser of the HP synthesis section (usually referred to as HPCC). Alternatively, the steam can be raised by evaporation of water from urea solution, e.g. downstream of the purification step, such as with re-boiling. The stripping is preferably carried out at a pressure of less than 3 bar (absolute). An advantage of steam stripping is stripping effect by the low partial ammonia vapour pressure, preferably in addition maintaining a high vapor pressure of water to reduce water evaporation. Some advantages of direct steam stripping with externally supplied steam are that dilution of the urea solution with water is useful for making DEF, and that downstream re-boiling of urea solution causing biuret formation can be avoided.

The purification is for instance based on heating the solution, to cause ammonia evaporation, and preferably also involves reducing the partial $NH_3$ pressure of the gas phase by stripping and/or reducing the absolute pressure. As a result of the heating and preferred (absolute) pressure reduction, water is also evaporated. The DEF purification off-gas may comprise predominantly water vapour, e.g. more than 50 wt. %, more than 70 wt. %, more than 90 wt. %, or more than 99 wt. % water, and e.g. from 0.5 wt. % and/or up to 5 wt. % $NH_3$. In some embodiments, the DEF purification off-gas and/or DEF purification section condensate comprise $NH_3$ in an amount corresponding at least 0.010 wt. % and/or max. 5.0 wt. % of the aqueous urea stream received by the DEF purification section.

The purification for instance comprises steam stripping of the aqueous urea solution. Steam stripping typically involves direct injection of steam in the aqueous urea stream, typically in counter-current flow, such as with liquid flowing down and steam flowing up. The stream of steam preferably comprises at least 90 wt. % $H_2O$, more preferably at least 95 wt. % $H_2O$. The pressure of the steam as injected is for instance 1 to 30 bara, preferably 2 to 15, typically 2 to 6 bara. The purification step, preferably stripping, more preferably steam stripping, is carried out at preferably less than 3.0 bar, less than 2.0 bar, or less than 1.5 bara, more preferably 0.10-1.1 bara, e.g. at less than 1.0 bar absolute, for example at 0.010 to 0.50 bar, or at 0.4 to 0.5 bara. Such operating pressures are in particular used for the steam stripper. The process comprises e.g. expanding the urea solution at between 3 and 7 bar obtained from LP recovery, to the pressures of the stripping step at e.g. less than 1.5 bara. The steam stripper for DEF purification is for example a vessel configured for counter-current flow of steam and liquid, having a liquid inlet at the top and liquid outlet at the bottom, and steam inlet in the bottom part and gas outlet at the top. The vessel for instance comprises trays and/or a packing.

Preferably, the DEF purification section will generally comprise at least one of a steam stripper, a heater, and a combination of a flash separator and a heater. The choice is made based at least in part on the extent of fluctuations in ammonia percentage in the aqueous urea product stream to be treated. For example, if the amount of ammonia varies too much, a heater is preferred over a stripper due to its flexibility.

In case of using a heater particularly in a sub-atmospheric dissociation section, a relatively large amount of water is evaporated and ends up in the DEF purification condensate. Accordingly, the invention of sending at least part of the DEF purification condensate to the LP dissociation section, has a still greater benefit in the event that the DEF purification section comprises a DEF dissociation section operating on the basis of a heater. By further preference, in the production of DEF, heating can advantageously be provided by direct steam injection, since water is needed in the product anyway. To the extent that a steam condensate results in additional water in the DEF purification condensate, the present invention is particularly beneficial. For, taking into account the route of the DEF purification condensate via the LP dissociation section, such additional water is effectively allowed to be returned to the DEF treatment section, rather than affecting the water content in the carbamate recycle back to urea synthesis.

In an alternative embodiment, the purification is carried out in a rectifying column with or without stripping, operating at reduced pressure. The rectifying column comprises a heater at the bottom, preferably a shell-and-tube heat exchanger, and a rectifying section comprising a structured packed bed or trays.

The DEF purification results in obtaining a purified urea solution that is suitable to meet the purity requirements for DEF. In order to produce DEF, the purified urea solution is to be further diluted to the desired urea concentration of generally 30%-35%, typically 32%-33%, preferably 32.5%. It will be understood that this dilution is conducted with water of such a quality as to not resulting in the introduction of new impurities, typically demineralized water or distilled water, or—advantageously—a purified process condensate. The latter may particularly be useful in the event of producing DEF in urea production plant that comprises a waste water treatment section.

From the DEF purification a DEF purification off-gas results. This is subjected to condensation, thereby obtaining a DEF purification condensate. As discussed above, in accordance with the invention, the process comprises sending DEF purification condensate to an LP dissociation section. This presents the advantageous choice that enables reducing the amount of water returned to urea synthesis via the LP condensation section, and it recirculates water to a stage of the process in which, eventually, the urea aqueous solution from which DEF is produced will be diluted anyway, thus reducing the amount of demineralized or distilled water required.

It will be understood that the presence of water in the LP condensation section cannot be altogether avoided. As the skilled person knows, for preventing crystallization of ammonium carbamate, a sufficient amount of water needs to be present. This can generally be provided from the urea plant's wastewater treatment section, such as by a lean carbamate solution (i.e. an aqueous ammonium carbamate solution generally containing less than 30 wt. % of ammonium carbamate, preferably more than 8 wt. %, more preferably between 15 wt. % and 25 wt. % of ammonium carbamate), obtained as a condensate from gaseous components obtained from wastewater treatment. In the aforementioned prior art processes involving a DEF purification treatment, the required amount of water is included in the water sent to the LP condensation section in the form of the DEF purification condensate. If desired, in the present invention the amount of water required in the LP condensation section can still be provided by part of the DEF purification condensate. In that event, the latter condensate will be split into a portion that is sent, in accordance with the invention, to the LP dissociation section, and a portion that is sent to the LP condensation section. Accordingly, in the process of the invention at least part of the DEF purification condensate is sent to an LP dissociation section, and possibly all of it. Preferably, at least 20-30 wt. % of the DEF purification condensate is sent to the LP dissociation section. The split ratio between the stream sent to the LP dissociation section and the stream sent to the LP condensation section is determined taking into account the amount of water required to prevent crystallization in the LP condensation section. Specifically, at the preferred conditions of the LP condensation section, there should be about 32 to 35 wt. % water in said section. If the amount of water is lower than this, then an additional source of process water can be routinely provided to the LP condensation section, in order to enable part of the DEF purification condensate to be sent to the LP dissociation section.

In another aspect, the invention also pertains to a plant for the production of DEF. Said plant serves to produce urea and to produce DEF therefrom, optionally in addition to other urea products. In order to produce urea, the plant comprises a high pressure (HP) synthesis section configured to subject ammonia and carbon dioxide to reaction under urea-forming conditions, thereby obtaining a urea synthesis solution. In order to provide a recycle of ammonium carbamate, the plant comprises; downstream of the HP synthesis section, and in fluid communication therewith, a low pressure (LP) recovery section. This section is configured to subject a passing urea solution to recovery of remaining ammonia and carbon dioxide contained therein. Said LP recovery section comprises an LP dissociation section and an LP condensation section. In order to receive the urea solution to be subjected to dissociation of ammonium carbamate contained therein, said LP dissociation section comprises an inlet for a urea solution, which inlet is in fluid communication with an outlet for a urea synthesis solution from the HP synthesis section. Such fluid communication can be directly from the HP synthesis section, or, optionally via one or more other sections positioned in between the HP synthesis section and the LP dissociation section, such as an MP section, particularly an MP recovery section that may comprise an MP dissociator, optionally an MP stripper, and from which the urea synthesis solution is obtained in an already partially purified form, and an MP ammonium carbonate condensate that can, directly or indirectly, be recycled to urea synthesis. The optional presence of an MP section, and the possible units and components thereof, do not require further elucidation to the skilled person.

The LP dissociation section comprises an outlet for an aqueous urea product stream, and an outlet for dissociation off-gas. In order to allow recycle of said off-gas as liquid carbamate, the outlet for dissociation off-gas is in fluid communication with a gas inlet of the LP condensation section, which section in turn has an outlet for LP condensate, which outlet is, directly or indirectly, in fluid communication with an inlet of the HP synthesis section.

The plant further comprising a DEF purification section. This section has an inlet for a liquid urea stream, in fluid communication with an outlet for an aqueous urea product stream of the LP dissociation section. The DEF purification section, as substantially discussed above, is configured to subject the aqueous urea product stream to removal of further ammonia.

The DEF purification section thereby has an outlet for a purified urea solution, which solution can be further treated, typically diluted, to obtain DEF at the desired concentration. Particularly, the DEF purification section has an outlet for DEF purification off-gas, which outlet is in fluid communication with an inlet of a DEF purification condensation section. The latter section is configured to subject the DEF purification off-gas to condensation, thereby obtaining a DEF purification condensate. In accordance with invention, said DEF purification condensation section is connected with the LP dissociation section.

To this end, the DEF purification condensation section has an outlet for DEF purification condensate, which outlet is in fluid communication with an inlet of the LP dissociation section. It will be understood that this refers to an inlet in such a position as to allow subjecting at least part of the DEF purification condensate to removal of ammonia in the LP dissociation section. This can be the same inlet as that for the urea synthesis solution sent to the LP dissociation section, or a different inlet. The inlet for the DEF purification condensate into the LP dissociation section can be parallel to the inlet for said urea synthesis solution, downstream thereof, or upstream thereof (thereby first allowing the DEF purification condensate to be combined with the urea synthesis solution, such as via a T connection).

In a further aspect, the invention pertains to a method of modifying a pre-existing plant for the production of an aqueous urea solution suitable for use as a Diesel Exhaust Fluid (DEF). Said pre-existing plant will generally comprise an HP synthesis section, optionally an MP recovery section, and an LP recovery section as described above, and as customary in the field. Being a plant for the production of DEF, the pre-existing plant will further comprising a DEF purification section. The latter section is configured to receive an aqueous urea product stream from an LP dissociation section, it will have an outlet for a purified urea solution, and an outlet for DEF purification off-gas. The latter outlet is in fluid communication with an inlet of a DEF purification condensation section configured to subject the DEF purification off-gas to condensation, thereby obtaining a DEF purification condensate. Said DEF purification, in a pre-existing plant, may have an outlet for DEF purification condensate, which outlet is in fluid communication with the LP recovery section, viz. to an LP condensation section thereof. The modification method of the present invention comprises providing a fluid connection from an outlet for the DEF purification condensate of the DEF purification condensation section, with an inlet for a urea solution into the LP dissociation section.

The invention also enables modifying a pre-existing urea production plant that is not a plant for the production of DEF. This refers to a urea production plant comprising a high pressure (HP) synthesis section configured to subject ammonia and carbon dioxide to reaction under urea-forming conditions, thereby obtaining a urea synthesis solution; downstream thereof and in fluid communication therewith, a low pressure (LP) recovery section configured to subject a passing urea solution to recovery of remaining ammonia and carbon dioxide contained therein, said LP recovery section comprising an LP dissociation section and an LP condensation section, said LP dissociation section comprising an inlet for a urea solution, said inlet being in fluid communication, optionally via an MP section, with an outlet for a urea synthesis solution from the HP synthesis section, an outlet for an aqueous urea product stream, and an outlet for dissociation off-gas, said outlet for dissociation off-gas being in fluid communication with a gas inlet of the LP condensation section, said LP condensation section having an outlet for LP condensate which outlet is in fluid communication with an inlet of the HP synthesis section.

The modification in accordance with the present invention comprises adding a DEF purification section as substantially discussed hereinbefore. This section is configured to subject the aqueous urea product stream to removal of further ammonia, said DEF purification section having an inlet for a liquid urea stream, which inlet is in fluid communication with the outlet for an aqueous urea product stream of the LP dissociation section, an outlet for a purified urea solution, and an outlet for DEF purification off-gas, said outlet for DEF purification off-gas being in fluid communication with an inlet of a DEF purification condensation section configured to subject the DEF purification off-gas to condensation, thereby obtaining a DEF purification condensate, said DEF purification condensation section having an outlet for said DEF purification condensate, which outlet is in fluid communication with an inlet of the LP dissociation section.

Various general preferences and specific embodiments are discussed with reference to the process aspect of the invention. Unless specified otherwise, these preferences and embodiments will be analogously applicable to the plant aspect of the invention, as well as to the aspects of modifying pre-existing plants.

The invention is further illustrated with reference to the drawing. It will be understood that the drawing is not limiting the invention. E.g., the invention is not limited to the specific types of equipment and specific plant systems as shown. The FIGURE shows schematically equipment parts and process streams relating to embodiments of the invention.

Referring to FIG. 1, $CO_2$ and $NH_3$ react under urea synthesis conditions in a urea synthesis section that operates at high pressure to produce a urea synthesis stream (1). The exemplified urea synthesis section includes an HP reaction zone (2) and an HP stripper (3).

The urea synthesis stream (1) is then sent to a Low pressure (LP) recovery section (4), where non-converted ammonia and carbon dioxide are recovered from the urea synthesis stream (1). By the expansion to low pressure, a portion of the carbamate left in urea synthesis stream (1) decomposes and evaporates. The remaining liquid is heated in an LP dissociation section (5), or otherwise subjected to a dissociation step (such as by flashing or by stripping) in order to further decompose carbamate. The vapor from the LP dissociation section (5) is condensed in an LP carbamate condensation section (6) and is recycled back to the urea synthesis section as an LP carbamate-containing condensate (7). The aqueous urea stream obtained from this LP dissociation section (8) is sent to a DEF production section (9).

The DEF production section (9) include a, preferably sub-atmospheric, dissociation section (LLPD) (10), in which ammonia is separated from aqueous urea stream (8) to give a purified urea solution (11) and a DEF purification off-gas (12). The purified urea solution (11) is then diluted by a demineralized or distilled water stream (16) to a suitable DEF concentration. The DEF purification off-gas (12) is sent to a DEF carbamate condensation section (13), where it is condensed to give a lean carbamate stream (14), viz., the DEF purification condensate. In the exemplified embodiment as depicted, a part of lean carbamate stream (14a) is sent to the LP dissociation section (5) and the remaining part (14b) is sent to the LPCC (6).

While the invention has been illustrated and described in detail in the drawings and foregoing description, such illustration and description are to be considered illustrative or exemplary and not restrictive; the invention is not limited to the disclosed embodiments.

For example, it is possible to operate the invention in an embodiment wherein more than one aqueous stream is separated from different places in or after the recovery section, to obtain the aqueous urea solution.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain features of the invention are recited in mutually different dependent claims does not indicate that a combination of these features cannot be used to advantage.

In sum, a process is disclosed for the production of an aqueous urea solution suitable for use as a Diesel Exhaust Fluid (DEF), wherein a condensate of off-gas obtained from further purifying an aqueous urea stream in a treatment section adapted to produce DEF, is sent to an LP dissociation section, thereby the removal of ammonia therefrom. This enables water obtained from such condensate to be recirculated to the DEF purification section, and prevents an unwanted build-up of water in recirculation to urea synthesis.

The invention claimed is:

1. A process for the production of an aqueous urea solution suitable for use as a Diesel Exhaust Fluid (DEF), the process comprising reacting ammonia and carbon dioxide in a high pressure (HP) synthesis section under urea-forming conditions, thereby obtaining a urea synthesis solution; subjecting the urea synthesis solution to a recovery treatment so as to remove remaining ammonia and carbon dioxide therefrom, said treatment comprising dissociation in a low pressure (LP) dissociation section, resulting in an aqueous urea product stream and an LP dissociation off-gas; subjecting said LP dissociation off-gas to condensation, thereby obtaining an LP condensate; recirculating said LP condensate as a feed to urea synthesis; subjecting the aqueous urea product stream to removal of further ammonia in a DEF purification section, thereby obtaining a purified urea solution and a DEF purification off-gas; subjecting the DEF purification off-gas to condensation thereby obtaining a DEF purification condensate; adjusting the water content of the purified urea solution, thereby obtaining a DEF product solution; wherein the process comprises subjecting at least part of the DEF purification condensate to removal of ammonia in the LP dissociation section.

2. The process according to claim 1, wherein the DEF purification section is operated under a pressure of from 0.1 barA to 2 barA.

3. The process according to claim 1, wherein the DEF purification section is operated at a sub-atmospheric pressure.

4. The process according to claim 3, wherein the pressure is in a range of from 0.3 barA to 0.6 barA.

5. The process according to claim 1, wherein adjusting the water content of the purified urea solution comprises dilution with water selected from the group consisting of demineralized water, distilled water, and mixtures thereof.

6. The process according to claim 1, wherein adjusting the water content of the purified urea solution comprises dilution with a purified process condensate.

7. The process according to claim 1, wherein the aqueous urea product stream has a urea concentration of 60 to 85 wt. %.

8. The process according to claim 1, wherein subjecting the aqueous urea product stream to removal of further ammonia in a DEF purification section comprises heating to a temperature below 135° C.

9. The process according to claim 8, wherein said heating comprises injecting steam into the aqueous urea product stream.

10. The process according to claim 1, wherein
   The DEF purification condensate is divided into a portion that is sent to the LP dissociation section, and a portion that is sent to an LP condensation section.

11. The process according to claim 1, wherein at least 20 wt. % of the DEF purification condensate, is sent to the LP dissociation section.

12. A plant for the production of an aqueous urea solution suitable for use as a Diesel Exhaust Fluid (DEF), said plant comprising a high pressure (HP) synthesis section configured to subject ammonia and carbon dioxide to reaction under urea-forming conditions, thereby obtaining a urea synthesis solution; downstream thereof and in fluid communication therewith, a low pressure (LP) recovery section configured to subject a passing urea solution to recovery of remaining ammonia and carbon dioxide contained therein, said LP recovery section comprising an LP dissociation section and an LP condensation section, said LP dissociation section comprising an inlet for a urea solution, said inlet being in fluid communication, optionally via an MP section, with an outlet for a urea synthesis solution from the HP synthesis section, an outlet for an aqueous urea product stream, and an outlet for dissociation off-gas, said outlet for dissociation off-gas being in fluid communication with a gas inlet of the LP condensation section, said LP condensation section having an outlet for LP condensate which outlet is in fluid communication with an inlet of the HP synthesis section; the plant further comprising a DEF purification section configured to subject the aqueous urea product stream to removal of further ammonia, said DEF purification section having an inlet for a liquid urea stream, which inlet is in fluid communication with the outlet for an aqueous urea product stream of the LP dissociation section, an outlet for a purified urea solution, and an outlet for DEF purification off-gas, said outlet for DEF purification off-gas being in fluid communication with an inlet of a DEF purification condensation section configured to subject the DEF purification off-gas to condensation, thereby obtaining a DEF purification condensate, said DEF purification condensation section having an outlet for said DEF purification condensate, which outlet is in fluid communication with an inlet of the LP dissociation section.

13. A method of modifying a pre-existing plant for the production of an aqueous urea solution suitable for use as a Diesel Exhaust Fluid (DEF), said pre-existing plant comprising a high pressure (HP) synthesis section configured to subject ammonia and carbon dioxide to reaction under urea-forming conditions, thereby obtaining a urea synthesis solution; downstream thereof and in fluid communication therewith, a low pressure (LP) recovery section configured to subject a passing urea solution to recovery of remaining ammonia and carbon dioxide contained therein, said LP recovery section comprising an LP dissociation section and an LP condensation section, said LP dissociation section comprising an inlet for a urea solution, said inlet being in fluid communication with an outlet for a urea synthesis solution from the HP synthesis section, an outlet for an aqueous urea product stream, and an outlet for dissociation off-gas, said outlet for dissociation off-gas being in fluid communication with a gas inlet of the LP condensation section, said LP condensation section having an outlet for LP condensate which outlet is in fluid communication with an inlet of the HP synthesis section; the plant further comprising a DEF purification section configured to subject the aqueous urea product stream to removal of further ammonia, said DEF purification section having an inlet for a liquid urea stream, which inlet is in fluid communication with the outlet for an aqueous urea product stream of the LP dissociation section, an outlet for a purified urea solution, and an outlet for DEF purification off-gas, said outlet for DEF purification off-gas being in fluid communication with an inlet of a DEF purification condensation section configured to subject the DEF purification off-gas to condensation, thereby obtaining a DEF purification condensate, said DEF purification condensation section having an outlet for said DEF purification condensate, which outlet is in fluid communication with the LP recovery section, the method comprising providing a fluid connection between an outlet for the DEF purification condensate of the DEF purification condensation section, with an inlet for a urea solution of the LP dissociation section.

14. A method of modifying a pre-existing urea production plant comprising a high pressure (HP) synthesis section configured to subject ammonia and carbon dioxide to reaction under urea-forming conditions, thereby obtaining a urea synthesis solution; downstream thereof and in fluid communication therewith, a low pressure (LP) recovery section configured to subject a passing urea solution to recovery of remaining ammonia and carbon dioxide contained therein, said LP recovery section comprising an LP dissociation section and an LP condensation section, said LP dissociation section comprising an inlet for a urea solution, said inlet being in fluid communication, optionally via an MP section, with an outlet for a urea synthesis solution from the HP synthesis section, an outlet for an aqueous urea product stream, and an outlet for dissociation off-gas, said outlet for dissociation off-gas being in fluid communication with a gas inlet of the LP condensation section, said LP condensation section having an outlet for LP condensate which outlet is in fluid communication with an inlet of the HP synthesis section, the method comprising adding a DEF purification section configured to subject the aqueous urea product stream to removal of further ammonia, said DEF purification section having an inlet for a liquid urea stream, which inlet is in fluid communication with the outlet for an aqueous urea product stream of the LP dissociation section, an outlet for a purified urea solution, and an outlet for DEF purification off-gas, said outlet for DEF purification off-gas being in fluid communication with an inlet of a DEF purification condensation section configured to subject the DEF purification off-gas to condensation, thereby obtaining a DEF purification condensate, said DEF purification condensation section having an outlet for said DEF purification condensate, which outlet is in fluid communication with an inlet of the LP dissociation section.

15. The process according to claim 1, wherein the DEF purification section is operated under a pressure of from 0.1 barA to 1.0 barA.

16. The process according to claim 1, wherein the aqueous urea product stream has a urea concentration of 60 to 77 wt. %.

17. The process according to claim 1, wherein subjecting the aqueous urea product stream to removal of further ammonia in a DEF purification section comprises heating to a temperature not exceeding 100° C.

18. The process according to claim 1, wherein at least 30 wt. % of the DEF purification condensate, is sent to the LP dissociation section.

* * * * *